United States Patent
Cichos et al.

(10) Patent No.: US 9,360,416 B2
(45) Date of Patent: Jun. 7, 2016

(54) TWIN-FOCUS PHOTOTHERMAL CORRELATION SPECTROSCOPY METHOD AND DEVICE FOR THE CHARACTERIZATION OF DYNAMICAL PROCESSES IN LIQUIDS AND BIOMATERIALS WITH THE HELP OF ABSORBING MARKERS

(75) Inventors: Frank Cichos, Berlin (DE); Marco Braun, Leipzig (DE); Markus Selmke, Leipzig (DE); Romy Schachoff, Leipzig (DE)

(73) Assignee: Universität Leipzig, Leipzig (DE)

( * ) Notice: Subject to any disclaimer, the term of this patent is extended or adjusted under 35 U.S.C. 154(b) by 72 days.

(21) Appl. No.: 14/232,304
(22) PCT Filed: Jul. 12, 2012
(86) PCT No.: PCT/EP2012/063741
§ 371 (c)(1),
(2), (4) Date: Apr. 6, 2014
(87) PCT Pub. No.: WO2013/007804
PCT Pub. Date: Jan. 17, 2013

(65) Prior Publication Data
US 2015/0036145 A1 Feb. 5, 2015

(30) Foreign Application Priority Data
Jul. 13, 2011 (EP) .................................. 11173831

(51) Int. Cl.
*G01N 21/00* (2006.01)
*G01N 21/31* (2006.01)
(Continued)

(52) U.S. Cl.
CPC ................ *G01N 21/31* (2013.01); *B82Y 15/00* (2013.01); *G01N 21/171* (2013.01); *G01N 33/487* (2013.01); *G01N 2021/1789* (2013.01)

(58) Field of Classification Search
CPC ....... G01N 21/64; G01N 21/71; G01N 25/00; G01J 5/0825

USPC ................. 356/432–440, 300, 318, 319, 417; 374/4, 7, 57; 250/341.6, 341.4, 358.1, 250/360.1
See application file for complete search history.

(56) References Cited

U.S. PATENT DOCUMENTS 5,118,945 A * 6/1992 Winschuh et al. ......... 250/341.4
6,756,591 B1   6/2004 Lounis et al.
(Continued)

FOREIGN PATENT DOCUMENTS

WO 2004/025278 A1 3/2004
WO 2006/013272 A2 2/2006
WO 2009/150526 A2 12/2009

OTHER PUBLICATIONS

Seisenberger G. et al.: Real-Time Single-Molecule Imaging of the Infection Pathway of an Adeno-Associated Virus; Science 294 (2001) 1929.
Haustein E. et al.: Ultrasensitive investigations of biological systems by fluorescence correlation spectroscopy. Methods 29 (2003) 153-166.
(Continued)

*Primary Examiner* — Hoa Pham
(74) *Attorney, Agent, or Firm* — Gudrun E. Huckett (57) ABSTRACT

The invention relates to a method and a device for twin-focus photothermal correlation spectroscopy for the characterization of dynamical processes in liquids and biomaterials with the help of absorbing markers. Thereby non-fluorescent absorbing nano objects are heated by an intensity-modulated heating laser which leads to a refractive index gradient lens around the object. This refractive index gradient is detected by a detection laser with a focal volume that, depending on the position of the heated object relative to the focal plane of the detection beam, splits into two-sub-volumes forming a twin-focus comprising two sharply separated parts of a focal volume showing no spatial overlap.

11 Claims, 5 Drawing Sheets

(51) Int. Cl.
*G01N 21/17* (2006.01)
*B82Y 15/00* (2011.01)
*G01N 33/487* (2006.01)

(56) References Cited

U.S. PATENT DOCUMENTS

| | | | |
|---|---|---|---|
| 7,036,979 B2 * | 5/2006 | Mawatari | 374/130 |
| 7,142,305 B2 * | 11/2006 | Yamaguchi | B01J 19/0093 356/432 |
| 7,894,067 B2 * | 2/2011 | Hell | 356/417 |
| 2004/0052292 A1 * | 3/2004 | Lounis et al. | 374/43 |
| 2006/0109465 A1 * | 5/2006 | Fukuzawa | G01N 21/645 356/417 |
| 2010/0252750 A1 * | 10/2010 | Xie et al. | 250/459.1 |
| 2011/0226962 A1 * | 9/2011 | Boudreau et al. | 250/459.1 |

OTHER PUBLICATIONS

Berciaud S. et al: Photothermal Heterodyne Imaging of Individual Nonfluorescent Nanoclusters and Nanocrystals. Phys. Rev. Lett. 93 (2004) 257402.
Lasne D. et al.: Single Nanoparticle Photothermal Tracking (SNaPT) of 5-nm Gold Beads in Live Cells. Biophysical Journal, vol. 91 (2006) 4598-4606.
Radünz R. et al.: Hot Brownian Particles and Photothermal Correlation Spectroscopy. J. Phys. Chem. A 113 (2009) 1674.
Paulo P.M.R. et al.: Photothermal Correlation Spectroscopy of Gold Nanoparticles in Solution. J.Phys.Chem. C 112 (2009) 11451-11457.
Octeau V. et al.: Photothermal absorption correlation spectroscopy. ACS Nano, 3(2):345-50 (2009).
Müller C. B. et al.: Dual-focus fluorescence correlation spectroscopy of colloidal solutions: influence of particle size. J. Phys. Chem. B 112 (2008) 8236-8240.

* cited by examiner

TWIN-FOCUS PHOTOTHERMAL CORRELATION SPECTROSCOPY METHOD AND DEVICE FOR THE CHARACTERIZATION OF DYNAMICAL PROCESSES IN LIQUIDS AND BIOMATERIALS WITH THE HELP OF ABSORBING MARKERS

BACKGROUND OF THE INVENTION

The method according to the invention allows the measurement of dynamical processes in liquids, liquid mixtures and complex soft materials such as biological materials or living cells with the help of a split focal volume (twin focus) in photothermal detection, in particular in photothermal correlation spectroscopy. The well separated focal volumes, precisely sub-volumes show no spatial overlap and thus allow the study of isotropic as well as anisotropic processes in biophysics, biology, physics, chemistry and medicine (e.g. high throughput screening).

Recent developments in the field of optical microscopy and detector technology have given access to the fluorescence of single molecules allowing to study dynamical processes on the nanoscale. This has become especially important in the field of biophysics/biochemistry where single fluorescent molecules are used as markers/tracers to follow biologically relevant processes. The most promising applications involve the detection of dynamical processes in living cells such as the infection pathways a virus takes entering the cell and cell nucleus [1], as single molecule techniques provide local information due to the small size of the markers (nanometer scale). During the approximately 20 years of single molecule fluorescence detection a large number of different experimental techniques have been developed. An especially useful variant of fluorescence detection is fluorescence correlation spectroscopy (FCS) [2]. Commonly, FCS is employed in the context of confocal or multi-photon excitation microscopy. In these techniques light is focused on a sample and the measured fluorescence intensity fluctuations (due to diffusion, physical or chemical reactions, aggregation, etc.) are recorded and analyzed using the temporal autocorrelation. Because the measured property is essentially related to the magnitude and/or the amount of fluctuations, there is an optimum measurement regime at the level when individual species enter or exit the observation volume (or turn on and off in the volume). When too many entities are measured at the same time the overall fluctuations are small in comparison to the total signal and may not be resolvable—in the other direction, if the individual fluctuation-events are too sparse in time, one measurement may take prohibitively too long. FCS is in a way the fluorescent counterpart to dynamic light scattering, which uses coherent light scattering, instead of (incoherent) fluorescence.

When an appropriate model for the analysis of the temporal autocorrelation is known, FCS can be used to obtain quantitative information such as
- diffusion coefficients
- hydrodynamic radii
- average concentrations
- kinetic chemical reaction rates
- singlet-triplet dynamics
- molecular binding kinetics
- molecular binding constants.

As fluorescent markers come in a variety of colors and can be specifically bound to a particular molecule (e.g. proteins, polymers, metal-complexes, etc.), it is possible to study the behavior of individual molecules. With the development of sensitive detectors such as avalanche photodiodes the detection of the fluorescence signal coming from individual molecules in highly dilute samples has become practical. With this emerged the possibility to conduct FCS experiments in a wide variety of specimens, ranging from materials science to biology. The advent of engineered cells with genetically tagged proteins (like green fluorescent protein) has made FCS a common tool for studying molecular dynamics in living cells.

Despite these successful applications, FCS suffers from a number of drawbacks, which are either due to the use of organic chromophores itself or due to technical limitations set by the optical detection and excitation scheme used in confocal microscopy.

The drawbacks of organic chromophores, fluorescent probes or semiconductor quantum dots are related to the following facts
- dye molecules have to be specifically designed especially in the case when they shall be bound to biological structures
- dye molecules need to have a large emission quantum yield, which however depends on the local environment
- dye molecules shall not undergo chemical reactions with molecular species involved in the processes under investigation
- dye molecules as fluorescent markers/tracer shall not interfere with the function of molecular species they tag
- dye molecules undergo photochemical processes which lead to an irreversible bleaching
- dye molecules obey a complex intermittent emission behavior known as blinking, which prevents the emission of photons during time period between microseconds and seconds
- dye molecules have a limited photon emission rate.

These drawbacks of organic fluorescent marker molecules have been resolved by employing absorbing particles instead of organic dye molecules. Absorbing particles do not suffer from most of the photophysical limitations described above. However, as they do not emit fluorescence photons they cannot be detected in fluorescence microscopy. Thus other techniques for the detection of single absorbing particles have been developed. Among the direct detection by light scattering, small particles below a size of a few 10 nm are not visible in light scattering microscopy especially in inhomogeneous environments such as living cells. A relatively new detection method for single absorbing nanoparticles is photothermal microscopy [3]. Photothermal detection techniques employ an optical heating of particles in a confocal microscope and the release of heat from these particles for their detection. The released heat induces a local refractive index change, which is monitored by a second focused laser, which is not absorbed by the particle. Such photothermal detection methods have, for example, already been used to track single gold particles in solution [4].

Above that, the WO 2004/025278 A1 describes a photothermal detection method based on a dual laser focus and differential interference contrast. In this method two laterally displaced focal volumes are used to probe the dynamics of a particle for random and oriented motion. Thereby, the two focused laser beams are spatially separated before they pass through the sample. In this way, both lasers experience a different phase shift as they interact, or not, with the sample, precisely with the thermally induced refractive index variation. Subsequently, the two laser beams are brought to interfere on an appropriate detector, whereby the detected signal intensity depends on the phase difference between the lasers.

Because of the lateral displacement of the laser foci and the need to separate the detection lasers in probe and reference beam, this method is not easy to integrate in a microscopic setup. Furthermore, the diffraction-limited laser beams will always overlap which leads to an uncertainty when it comes to the detection of directed motion. Spatial information on the position of a probe in one of the focal volumes itself can also not be obtained with this method.

As the heating of small particles can be carried out very quickly (MHz), lock-in techniques can be used to differentiate between scattering, and absorbing particles in the sample. These techniques have been demonstrated in a correlation spectroscopy mode (largely equivalent to FCS) as well and are termed photothermal correlation spectroscopy (PhoCS) [5].

Such photothermal correlation spectroscopy has, for example, already been used to analyze the free diffusion of gold nanoparticles in solution. Therefore, the correlations of an interferometric photothermal signal have been analyzed. In particular, the autocorrelation function of the time traces of the photothermal signal was determined and information about the diffusion dynamics of the absorbing particles across the focus has been obtained [6]. Furthermore, such method has been used for the precise determination of the hydrodynamic sizes of different functionalized gold nanoparticles [7]. Thus, in analogy to standard fluorescence correlation spectroscopy (FCS) the autocorrelation function cannot provide information about directed motion of the tested particles.

By using absorbing nanoparticles instead of organic dye molecules as described above, most of the chromophore related drawbacks of FCS have been removed. Still, technical drawbacks of FCS related to the confocal microscopy setup itself remain, especially the confocal detection volume is limited by diffraction and aberrations
the confocal detection volume is commonly modeled as an 3-dimensional gaussian volume
no spatial information on the position of the dye molecule in the focal volume is obtained
FCS delivers no information on anisotropic dynamics in the focal volume.

The latter drawbacks have been partly removed by techniques modifying the focal volume of fluorescence correlation spectroscopy. For instance, the capability to detect anisotropic or directed motion, which is extremely important for the detection of driven processes in living cells, is introduced in dual focus FCS techniques [5]. Here two laterally displaced detection volumes are employed simultaneously to identify the motion from one focal volume to the other. The used focal volumes do, however, overlap spatially and no well defined border between the focal volumes is possible. Thus, such FCS techniques are not able to discriminate sharply between the two focal volumes, which is especially important for the detection of small velocity directed motions or small amplitude fluctuations (i.e. the motion of a few 10 nm). This is one of the major drawbacks which are removed by the presented method of twin-focus photothermal correlation spectroscopy.

The detailed drawbacks of current methods are based on
the use of organic fluorescent probes
the detection of fluorescence photons.

SUMMARY OF THE INVENTION

The objective of the invention is to overcome these drawbacks. This objective is solved by the method of twin-focus photothermal correlation spectroscopy with a focal volume that splits into two sub-volumes forming a twin-focus volume comprising two sharply separated parts of a focal volume showing no spatial overlap. The objective is further solved by a device for twin-focus photothermal correlation spectroscopy comprising:

a.) a heating laser with an intensity preferably modulated at a frequency between 100 kHz and 10 MHz
b.) a detection laser preferably used in continuous wave (cw) mode,
whereas both lasers path are merged and focused by a first objective lens to the sample,
to generate a twin-focus volume both heating and detection laser focal plane overlap, preferably at the same focal point,
the collected detection laser light is imaged by a second detection or a second microscopy lens on a photo detector or a photodiode.

The following description and claims disclose further preferred embodiments of the invention.

Within the twin focus photothermal correlation spectroscopy approach according to the invention, the following drawbacks of fluorescence correlation spectroscopy are removed:

the need for specifically designed fluorescent molecules
the lack of long term photostability of the markers under investigation
the contribution of complex intermittent emission of the markers to the correlation signal
the lack of spatial information on the particle position
spatial overlap of detection volumes in multi-focus FCS approach.

The following sources of these drawbacks are eliminated by the invention
the use of fluorescent probes
the use of fluorescence microscopy
the specific generation of multiple focal volumes for the detection of anisotropic motion.

Figure 1:
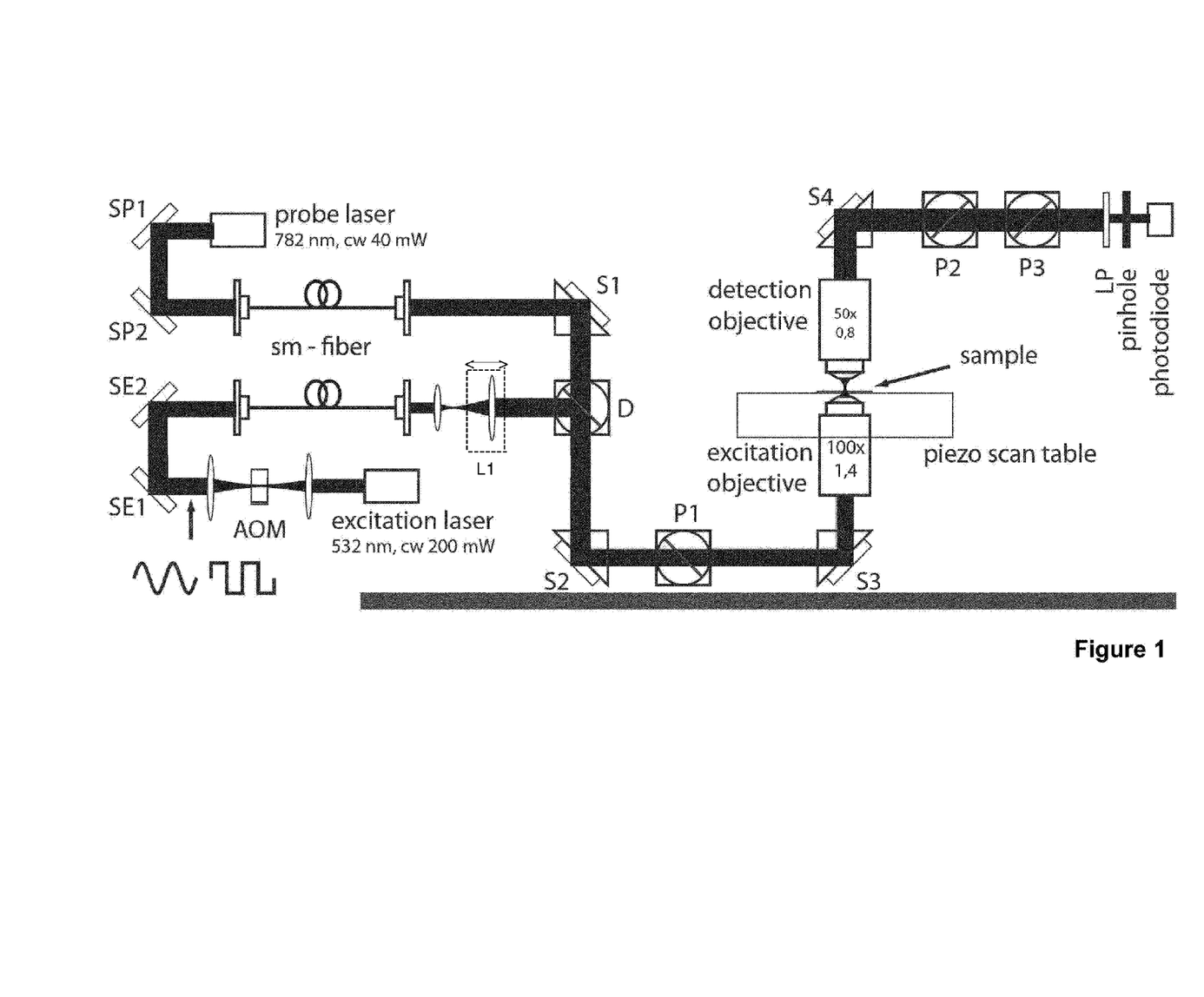
FIG. 1: Example of a photothermal microscopy setup for twin focus photothermal correlation spectroscopy.

The method according to the invention is based on single molecule photothermal microscopy methods as developed by Lounis and others [9-11]. It preferably employs a photothermal microscopy setup in transmission configuration as shown in FIG. 1. The device according to the invention comprises two lasers sources, which are used as the light sources for heating the absorbing nano objects (in the following called heating laser or excitation laser), e.g. nano particles or molecules, and detecting a change in the refractive index around the heat releasing nano object (in the following called detection laser or probe laser). The heating laser is intensity modulated at a frequency between 100 kHz and 1 MHz and preferable up to 10 MHz. The detection laser is used in continuous wave (cw) mode. Both lasers paths are merged and focused by an objective lens to the sample. To generate a twin focus volume (see Figure) both heating and detection laser focal volume have to overlap, in a preferred embodiment both heating and detection laser focal plane have to overlap at the same focal point.

An absorbing nano object, e.g. a particle, entering this focal volume of the heating laser will cause a divergent gradient index thermal lens around the object, resp. the particle. Depending on the position of the nano object, e.g. the particle, with respect to the focus of the detection laser, the detection beam will become either wider or narrower. The collected detection laser light, which is imaged by a detection lens, e.g. a second microscopy objective lens, on a photo detector, e.g. a photodiode, is thus either decreased or increased.

As the heating laser is modulated in intensity the detection laser scattering signal, and so the intensity at the photodetector, will become modulated as well, however, only if a nano object, e.g. a particle, including the thermal lens is in the focus of the detection laser. Thus the signal of the photo detector, e.g. a photodiode, can be analyzed at the heating laser intensity modulation frequency, for example by a lock-in amplifier, to remove unmodulated contributions when no nano object, e.g. no particle, is in the focus.

In this example, the lock-in amplifier will provide the amplitude and information about the relative phase of the detection intensity modulation to the heating laser intensity modulation. The phase information will provide the required information on the position of the nano object, e.g. a particle, in one of the two parts of the focal volume. While the photothermal microscopy technique has been known and applied so far, the lens like action and the splitting of the focal volume into two sub-volumes (twin focus) has not been known on a single particle level so far.

In the context of the twin focus photothermal correlation spectroscopy approach described here, the twin focus volume refers to the focal volume of the detection laser that splits into two sub-volumes in the presence of a heated nano object. Thereby, the twin focus differs from the already known dual focus methods, as the twin focal volumes, precisely the sub-volumes, show no spatial overlap but also no spatial gap between each other. On the contrary, they are adjacent to each other and together they form the focal volume of the detection laser.

As the heated nano object acts as a divergent gradient index thermal lens, the beam of the detection laser is configured depending on the relative position of the nano object and the focal plane of the detection beam. When the nano object is in propagation direction of the detection laser in front of its focal plane, the lens-like action of the nano object narrows the beam of the detection laser at the aperture of the detection lens. Respectively, for a position of the nano object behind the focal plane of the detection laser in its propagation direction the beam is widened. Thereby, the intensity of the detection laser on the photo detector is increased in the first (positive signal) and decreased in the second (negative signal) case. For a nano object in the focal plane of a non-aberrated detection laser the beam would neither be narrowed nor widened and thereby the signal neither increased nor decreased (see FIG. 5). In this way a focal volume that splits into two sub-volumes, the twin focus volumes, is generated. These neighboring volumes show no lateral or axial overlap. Consequently, they are well separated, as the modulation of the detection laser intensity modulation, the photothermal signal, shows a zero crossing when the nano object is in the focal plane of the detection laser.

When using a lock-in amplifier for the analysis of the photothermal signal, the magnitude and phase of the lock-in detected signal comprise the positive and negative signal parts. The signal amplitude and spatial size of the neighboring positive and negative sub-volumes is determined by the relative axial displacement of the heating and the detection laser beam focal planes. For example, in the case of non-aberrated heating and detection laser beams overlapping at the same focal point both negative and positive detection volumes will have the same size and signal magnitude. Adjusting the relative axial focal position of the heating to the detection laser beams allows enhancing either the positive or the negative photothermal signal.

Due to optical aberrations common to any microscope setup, the symmetric two lobe structure is not obtained for perfect heating and detection laser beam overlap. Further the particle position in the focal plane will cause a non-zero signal. The effect of the aberrations on symmetry of the detection volume can be compensated by changing the relative axial displacement of the focal planes of the detection and heating laser beam. In this way, by shifting the focal plane, one can not only counter the effects of aberration, but also cause an enhancement of either the positive or the negative signal. The axial offset of the two focal planes is adjusted by at least one additional lens in front of the objective, with which the divergence of either the heating or detection laser can be controlled.

The split focal volume with its, positive and negative signal parts is now allowing the detection of particle fluctuations in either one of the volumes or between the sub-volumes.

Thus the new technical component of our invention is based on the understanding of the signal generation in photothermal microscopy to provide the twin focus in single particle detection. In addition we supply the corresponding methods and models to analyze twin focus photothermal signals to measure dynamical processes in liquids and biological materials.

The invention comprises at least one of the following:
  a method of twin-focus photothermal correlation spectroscopy with a twin-focus volume comprising two separated focal volumes, precisely two sub-volumes, showing no spatial overlap.
  the experimental realization of two sharply separated focal volumes, precisely two sub-volumes, (two separated focal volumes, precisely two sub-volumes, showing no spatial overlap) for photothermal correlation spectroscopy
  the detection of phase sensitive signals from the two sharply separated focal volumes, precisely two sub-volumes, in photothermal correlation spectroscopy
  the experimental realization and application of two sharply separated parts, precisely sub-volumes, of a photothermal focal volume to detect anisotropic fluctuations in the concentration of absorbing non-fluorescent markers
  the experimental realization and application of two sharply separated parts, precisely sub-volumes, of a photothermal focal volume to detect directed dynamics of absorbing non-fluorescent markers along the optical axis of a photothermal microscope
  the experimental realization and application of two sharply separated parts, precisely sub-volumes, of a photothermal focal volume to detect spatial differences in the fluctuation of absorbing non-fluorescent markers in liquid and biological samples
  the analysis of the above mentioned processes by temporal correlation functions, which involve the autocorrelation and cross correlation of the signals from delivered by a lock-in amplifier Advantages of the invention include at least one of the following:
  intrinsic availability of two neighboring and sharply separated measurement volumes
  use of photostable marker/tracer nano objects e.g. of gold or other nobel metal nanoparticles
  measurement at medium light intensities with no requirement for photon counting detectors The non-fluorescent absorbing particles used as markers in the invention are preferably metal or metaloxid or carbon nanoparticles with a preferred diameter of 1 to 100 nm. The absorbing particles are preferably selected from gold or other noble metal nanoparticles, quantum dots or carbon nanotubes. The use of non-fluorescent absorbing molecules is possible as well.

Absorbing nano objects, e.g. particles or absorbing molecules (or light absorbing particles or molecules), mean in the context of the present invention that the nano objects absorb light and convert the absorbed energy at least to some extend into thermal energy, which results in a local heating around them. The local heating changes the refractive index that is detected by measuring the scattering of a laser beam.

Non-fluorescent nano objects, e.g. non-fluorescent particles or molecules, mean in the context of the present invention that the nano objects do not or only to a small extent re-emit the energy of the absorbed light in form of or light or electro-magnetic radiation. In particular the non-fluorescent nano objects are characterized by a quantum yield (as the ration of emitted photons per absorbed photons) smaller than 0.15, preferably smaller than 0.05 and mostly preferred smaller than 0.02.

The invention also comprises the use of the device according the invention and absorbing particles or molecules as described above to carry out the method according the invention.

DESCRIPTION OF PREFERRED EMBODIMENTS

Figure 3:
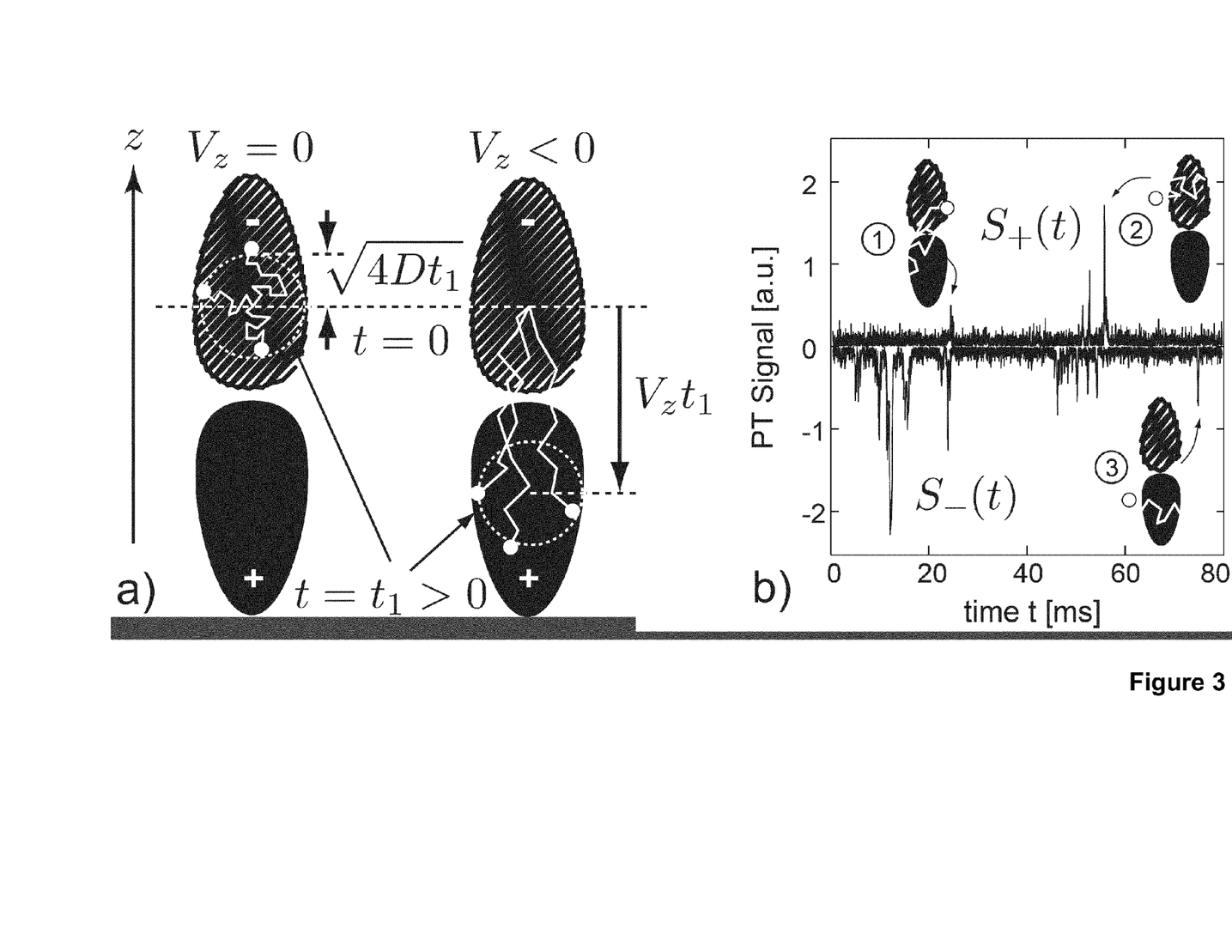
FIG. 3: Twin focus photothermal correlation spectroscopy time-trace (right) as well as different exemplary situations of events: (left) motion in one of the focal volume parts or sub-volumes, (second left) directed motion from one to the other volume parts, precisely from one to the other sub-volume.
Figure 4:
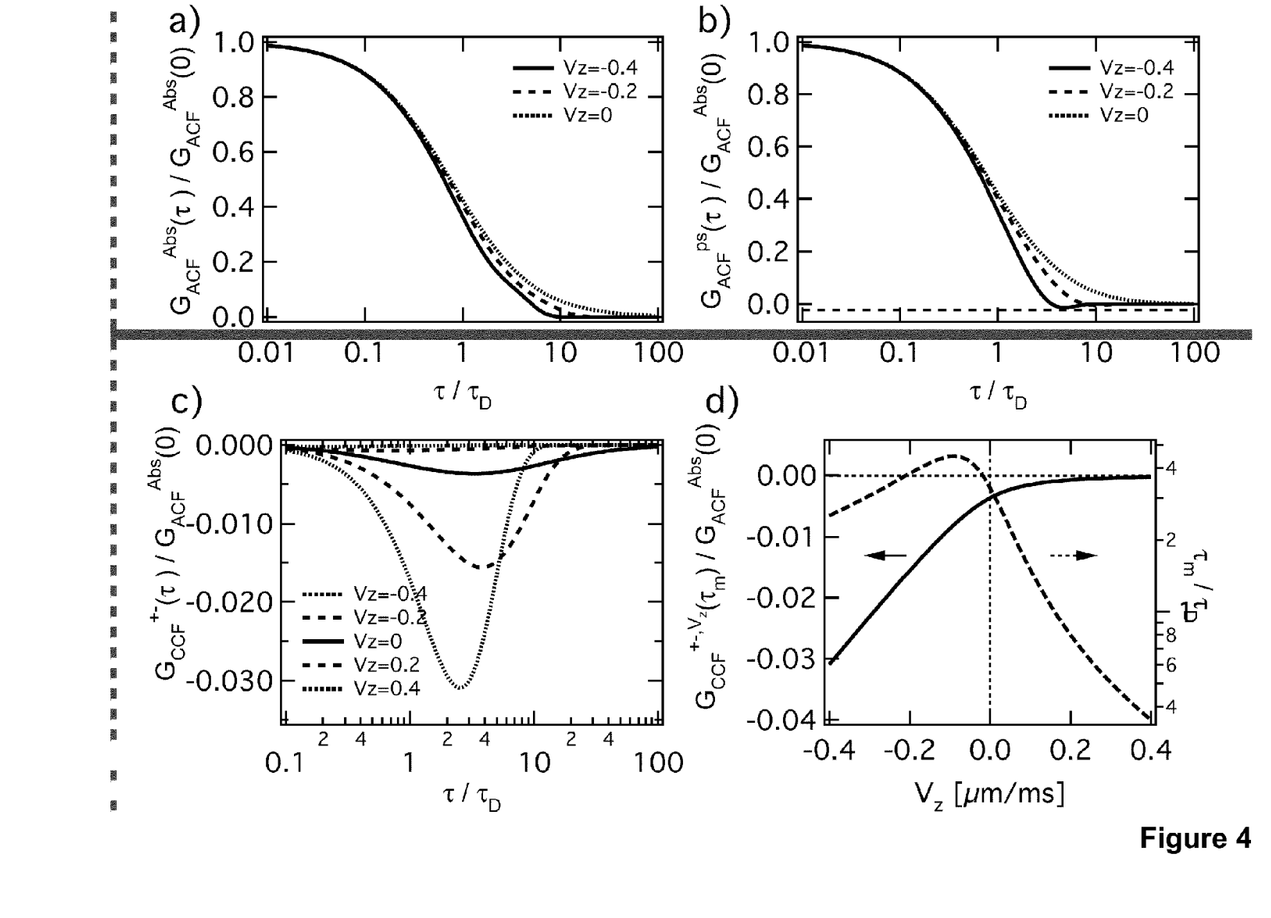
FIG. 4: Example twin focus photothermal correlation functions for different nanoparticle velocities (Vz) along the optical axis. The correlation functions show the temporal auto-correlation of the photothermal signal magnitude (top left), the temporal auto-correlation of the phase sensitive photothermal signal magnitude (top right) and the temporal cross correlation of the positive and negative parts of the phase sensitive signal as depicted in FIG. 3.
Figure 5:
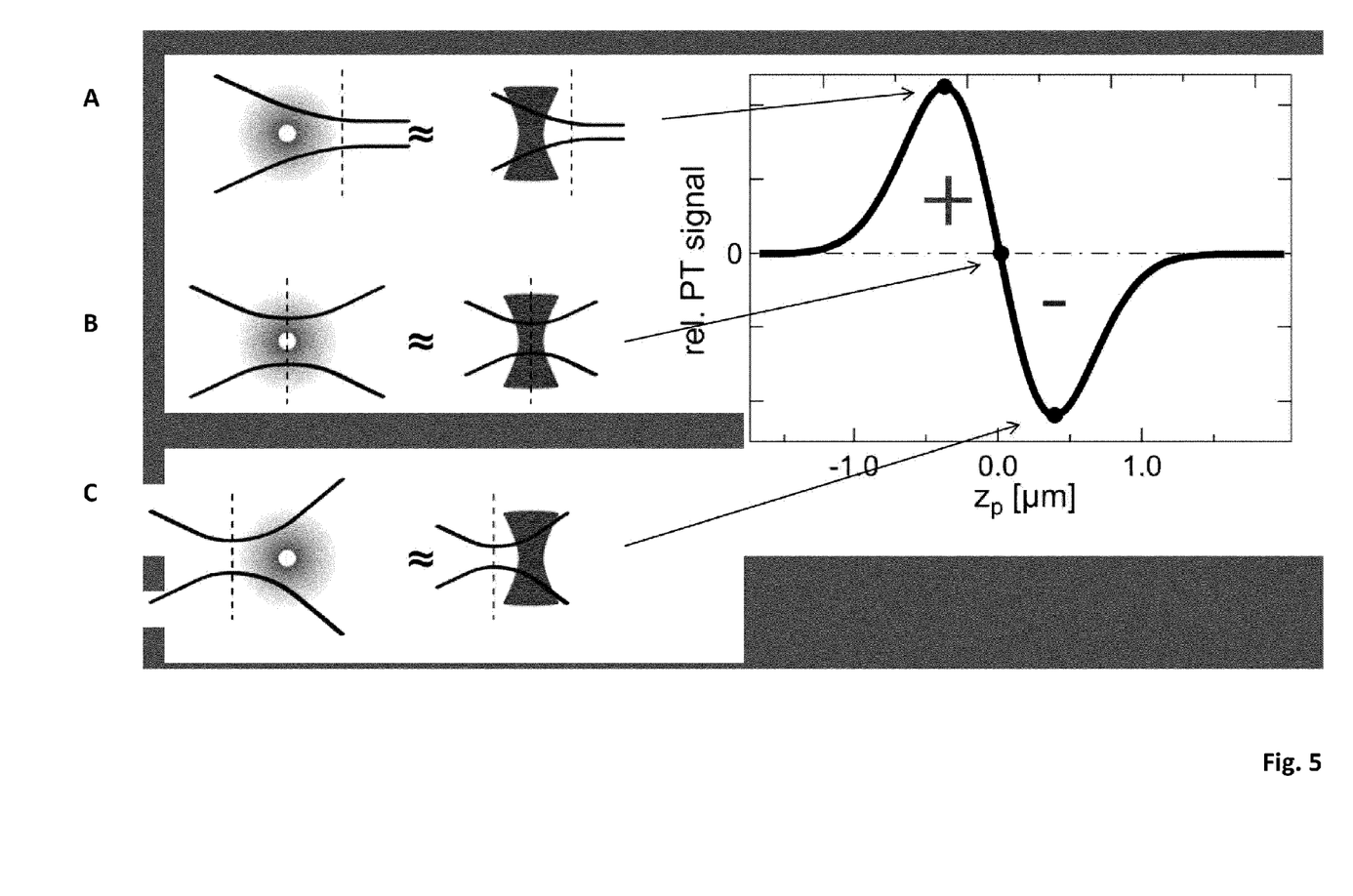
FIG. 5: Dependence of the detection laser beam divergence and the photothermal signal of the position of a heated particle. Thereby, (A) shows a heated particle that is in propagation direction of the detection laser in front of its focal plane, which leads to a narrower beam and an increased photothermal signal. Further, (B) shows a heated particle at the focal plane of the detection laser, which leads to a zero photothermal signal (for non-aberrated laser beams). Finally, (C) shows a heated particle behind the focal plane of the detection laser in its propagation direction, which leads to a wider beam and a decreased photothermal signal.

A detailed scheme of a photothermal microscopy setup for twin-focus photothermal correlation spectroscopy is depicted in FIG. 1. The setup has been used to image the twin focus photothermal volume as provided in FIG. 2. The twin-focus photothermal signal together with two examples of nanoparticle motion is depicted in FIG. 3. Corresponding exemplary temporal correlation functions as obtained from an analysis with the twin-focus photothermal correlation spectroscopy under directed motion of particles along the optical axis are shown in FIG. 4. The influence of the position of a heated particle relative to the focal plane of a detection laser with regard to the beam shape and the relative photothermal signal is depicted in FIG. 5 A-C.

In FIG. 1 the following abbreviations are used:
SP1, SP2: Mirrors for the probe laser, highly reflecting at the probe laser wavelength;
SE1, SE2: Mirrors for the excitation laser, highly reflecting at the excitation laser wavelength;
sm-fiber: single mode glass fiber for the probe or excitation wavelength;
AOM: acousto optic modulator, the acousto optic modulator is modulating the excitation intensity in a periodic fashion. The intensity modulation could be either sinusoidal or rectangular or any other periodic shape;
S1,S2,S3,S4: mirrors, highly reflecting over a wide wavelength region including the probe and excitation laser wavelength;
D: dichroic mirror, highly reflecting at the excitation laser wavelength and highly transmitting at the probe laser wavelength;
P1, P2, P3: Ports for reflecting out of the excitation, probe or transmitted beams at various positions of the setup;
L1: additional tense;
LP: long pass optical filter transmitting the probe laser wavelength and rejecting the excitation laser wavelength.

Figure 2:
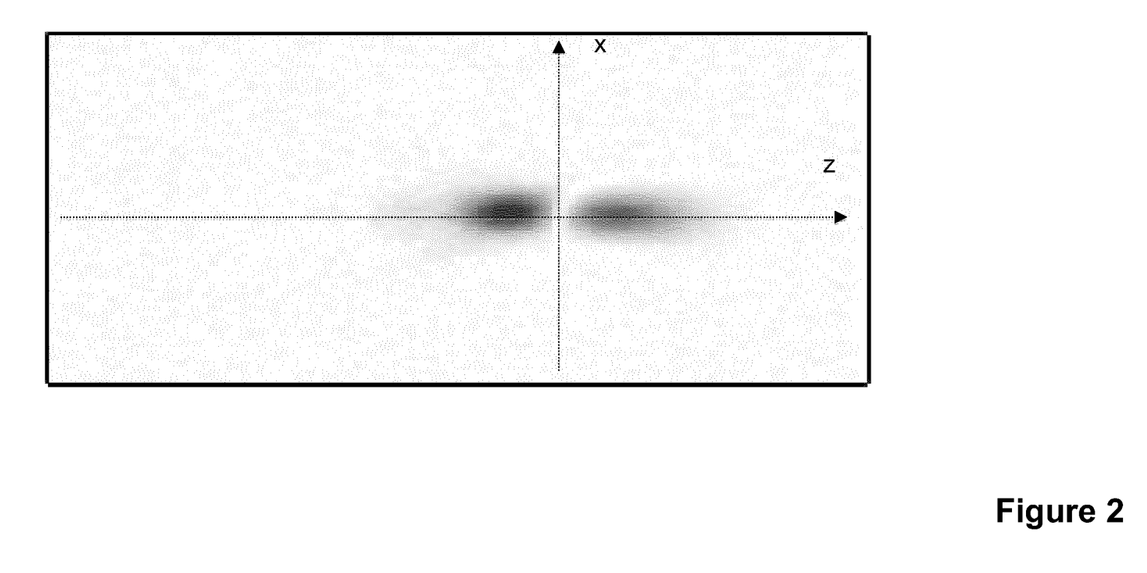
FIG. 2: Example of a twin focus photothermal detection volume along the optical axis of a photothermal microscope. The region left of the x-axis denote increased scattering signal and right of the x-axis denote decreased scattering signal and thus a different oscillation phase of the photothermal signal with respect to the phase of the modulated heating laser.

FIG. 2 shows photothermal signal of a R=30 nm gold nanoparticle in the x-z plane. The z-direction is the direction of the optical axis. The figure shows two lobes indicating the twin focus structure. Signal and distance are in arbitrary units.

FIG. 3 is an illustration of possible processes in twin-focus photothermal correlation spectroscopy (Twin-PhoCS) measurements. The two lobes are indicated with a "+" and a "−" corresponding to positive and negative photothermal signals, wherein it is shown in
   a) Left: simple Brownian motion of a sample particle/molecule in one of the twin focus lobes. $V_z=0$ indicates no drift velocity of the particle/molecule along the z-direction; t=0 denotes the starting time of the process. At a time $t_1$ after the Brownian motion has started, the particle/molecule has diffused a distance $\sqrt{4Dt_1}$
   Right: simple Brownian motion of a sample particle/molecule including a drift velocity $V_z<0$ in the negative z-direction. This causes the particle to change from the negative photothermal signal lobe to the positive photothermal signal lobe. The distance traveled due to the velocity $V_z$ is $V_z t_1$
   b) Experimental time trace for a R=30 nm gold nanoparticle displaying the positive $S_+(t)$ and the negative photothermal signal time trace. The illustrations 1-3 indicate individual events observed; 1: motion from one of the lobes to the other, 2: motion in the positive lobe, 3: motion in the negative lobe.

FIG. 4 shows examples for the different correlation functions, which may be calculated from the data obtained by the Twin-PhoCS method. The examples demonstrate the sensitivity of the different correlation function to a directional motion in z-direction (positive or negative velocity $V_z$). Graphs a)-c) show the dependence of the correlation function on the time $\tau$ for different values of the velocity in z-direction. Graph d) shows the minimum value of the $G_{CCF}^{+-}(\tau_m)$ and the temporal position $\tau_m$ (normalized to the average diffusion time $\tau_D$) where this minimum occurs as a function of the velocity $V_z$. In FIG. 4, the following parameters are shown:
$G_{ACF}^{Abs}(\tau)$ is the autocorrelation of the magnitude of the photothermal signal.

$G_{ACF}^{ps}(\tau)$ is the autocorrelation of the phase sensitive photothermal signal, where phase sensitive means, that the signal can be either positive or negative depending on the position of the particle/molecule in the lobe.

$G_{CCF}^{+-}(\tau_m)$ is the cross-correlation of the positive part with the negative part of the phase sensitive photothermal signal. $G_{CCF}^{+-}(\tau_m)$ is the value of cross-correlation of the positive part with the negative part of the phase sensitive photothermal signal at the time $\tau_m$ where the cross-correlation is minimum. $\tau_m$ is the time where the cross-correlation is minimum.

$\tau_D$ is the average diffusion time of the sample particle/molecule through the focal volume of the Twin-PhoCS setup.

$G_{ACF}^{Abs}(0)$ is the value of the autocorrelation function of the magnitude of the photothermal signal at $\tau=0$. This value is used to normalize all correlation functions.

FIG. 5 shows an illustration of the working principle of the twin focal volume effect used for the Twin-PhoCS method. The dot on the left side of the illustrations A, B, C depicts a sample particle/molecule which is surrounded by a temperature field and a refractive index gradient, respectively. The lines on the left side denote an incident probe laser beam focused on the particle/molecule. The dashed line represents the focal plane of the incident laser beam without the influence of the generated refractive index profile (nanolens). The two curved lines denote the shape of the probe laser beam modified by the nanolens. The illustration in the middle depicts the corresponding macroscopic analogue of the nanolens, which is a divergent lens.

In illustration A of FIG. 5, the focal plane of the probe laser is behind the created refractive index gradient corresponding to a beam focused to the back side of a divergent lens. The focus position of the incident beam is moved towards the detector, the sample beam is more convergent and the relative photothermal signal increases and is thus positive (right graph).

In illustration B of FIG. 5, the focal plane of the probe laser is at the position of the particle/molecule corresponding to a laser focused into the center of a divergent lens. This is not changing the position of the laser focus nor the divergence of the beam. The detected relative photothermal signal is therefore zero.

In illustration C of FIG. 5, the focal plane of the probe laser is in front of the created refractive index gradient corresponding to a beam focused to the front side of a divergent lens. The focus position of the incident beam is moved away from the detector, the sample beam is more divergent, and the relative photothermal signal increases and is negative (right graph).

The following references are cited within the description of the invention:

[1] Seisenberger, G., Ried, M. U., Endreβ, T., Büning, H., et al. Real-Time Single-Molecule Imaging of the Infection Pathway of an Adeno-Associated Virus. Science 294, 1929 (2001).

[2] Haustein, E. & Schwille, P. Ultrasensitive investigations of biological systems by fluorescence correlation spectroscopy. Methods 29, 153-166 (2003).

[3] Berciaud, S., Cognet, L., Blab, G. & Lounis, B. Photothermal Heterodyne Imaging of Individual Nonfluorescent Nanoclusters and Nanocrystals. Phys. Rev. Lett. 93, 257402 (2004).

[4] Lasne, D., Blab, G. A., Berciaud, S., Heine, M., Groc, L., Choquet, D., Cognet, L., Lounis, B. Single Nanoparticle Photothermal Tracking (SNaPT) of 5-nm Gold Beads in Live Cells. Biophysical Journal, Vol. 91, 4598-4606 (2006)

[5] Radünz, R., Rings, D., Kroy, K. & Cichos, F. Hot Brownian Particles and Photothermal Correlation Spectroscopy. J. Phys. Chem. A 113, 1674 (2009).

[6] Paulo, P. M. R., Gaiduk, A., Kulzer, F., Krens, S. F. G., Spaink, H. P., Schmidt, T., Orrit, M. Photothermal Correlation Spectroscopy of Gold Nanoparticles in Solution. J. Phys. Chem. C 112, 11451-11457 (2009)

[7] Octeau V, Cognet L, Duchesne L, Lasne D et al. Photothermal absorption correlation spectroscopy. ACS Nano, 3(2):345-50 (2009)

[8] Müller, C. B., Loman, A., Richtering, W. & Enderlein, J. Dual-focus fluorescence correlation spectroscopy of colloidal solutions: influence of particle size. J. Phys. Chem. B 112, 8236-8240 (2008).

[9] WO 2006/013272 A2

[10] WO 2004/025278 A1

[11] U.S. Pat. No. 6,756,591 B1

What is claimed is:

1. A method of twin-focus photothermal correlation spectroscopy, the method comprising:
   generating a detection laser focal volume that, in the presence of heated non-fluorescent particles as an absorbing marker, splits into two neighboring positive and negative sub-volumes forming a twin-focus volume comprising two sharply separated parts of the detection laser focal volume showing no spatial overlap by:
   focusing a detection laser beam and a heating laser beam by an objective lens;
   shifting a focal plane of the heating laser beam and a focal plane of the detection laser beam relative to each other by at least one additional lens arranged upstream of the objective lens to change a relative axial displacement of the focal planes of the detection laser beam and the heating laser beam relative to each other, the relative axial displacement determining a signal amplitude and a spatial size of the two neighboring positive and negative sub-volumes, wherein an intensity of the detection laser beam on a photo detector is either decreased or increased depending on a relative position of the heated non-fluorescent particles relative to the focal plane of the detection laser beam; and
   employing positive and negative signal parts of a detected photothermal signal of the twin-focus volume to detect fluctuations of the heated non-fluorescent particles in either one of the two neighboring positive and negative sub-volumes or between the two neighboring positive and negative sub-volumes.

2. The method according to claim 1, comprising detecting phase-sensitive signals from the two sharply separated parts of the detection laser focal volume.

3. The method according to claim 1, comprising detecting anisotropic fluctuations in the concentration of the heated non-fluorescent particles.

4. The method according to claim 1, comprising detecting directed dynamics of the heated non-fluorescent particles along an optical axis of a photothermal microscope.

5. The method according to claim 1, comprising analyzing the signal parts to obtain temporal correlation functions, wherein analyzing includes autocorrelation of the signal parts; cross correlation of the signal parts; or autocorrelation and cross correlation of the signal parts.

6. The method according to claim 1, wherein, depending on a position of the heated non-fluorescent particles comprising a divergent gradient index thermal lens around the heated non-fluorescent particles, the detection laser beam becomes either wider or narrower or remains unchanged and the detected photothermal signal either decreases or increases accordingly.

7. The method according to claim 1, comprising detecting an amplitude and a phase of the detection laser beam at a modulation frequency of the heating laser, the amplitude and the phase of the detection laser beam providing information on a position of the heated non-fluorescent particles in one of the two sharply separated parts of the detection laser focal volume.

8. The method according to claim 1, wherein an amplitude and a phase of the detection laser at the modulation frequency of the heating laser is detected to remove unmodulated contributions when no non-fluorescent particles are present in the detection laser focal volume.

9. A device for twin-focus photothermal correlation spectroscopy comprising:
- a heating laser with an intensity modulated at a frequency between 100 kHz and 10 MHz;
- a detection laser operated in continuous wave (cw) mode;
- an objective lens merging and focusing a laser path of the heating laser and a laser path of the detection laser onto a sample comprising non-fluorescent particles as an absorbing marker, wherein a focal plane of the heating laser and a focal plane of the detection laser overlap to generate a twin-focus volume;
- at least one additional lens arranged upstream of the objective lens and configured to adjust an axial offset of the focal plane of the heating laser and of the focal plane of the detection laser relative to each other, wherein the at least one additional lens controls a divergence of the heating laser; of the detection laser; or of the heating laser and the detection laser;
- a photo detector or a photodiode;
- a detection lens or a microscopy lens imaging collected detection laser light onto the photo detector or the photodiode.

10. The device according to claim 9, further comprising a lock-in amplifier enabling analysis of the signal of the photo detector or of the photodiode at the heating laser intensity modulation frequency and enabling removal of unmodulated contributions when no non-fluorescent particles are in the detection laser focal volume.

11. The device according to claim 10, wherein the lock-in amplifier is configured to detect a signal amplitude and a phase of the detection laser.

* * * * *